United States Patent [19]

Martinez-Pardo et al.

[11] Patent Number: 5,780,658
[45] Date of Patent: Jul. 14, 1998

[54] PROCESS FOR THE SYNTHESIS OF CATIONIC SURFACTANTS COMPRISING ESTERIFICATION WITH BASIC CHARACTER AMINO ACIDS

[75] Inventors: Marta Rosa Infante Martinez-Pardo; Augustin Contijoch Mestres; Pilar Erra Serrabasa, all of Barcelona, Spain

[73] Assignee: Laboratorios Miret, S.A., Barcelona, Spain

[21] Appl. No.: 704,684

[22] PCT Filed: Mar. 8, 1995

[86] PCT No.: PCT/ES95/00027

§ 371 Date: Sep. 10, 1996

§ 102(e) Date: Sep. 10, 1996

[87] PCT Pub. No.: WO96/21642

PCT Pub. Date: Jul. 18, 1996

[30] Foreign Application Priority Data

Jan. 10, 1995 [ES] Spain ..................... 9500061

[51] Int. Cl.$^6$ ............... C07C 277/08; C07C 231/02; C07C 279/14; A23L 3/35; A61K 7/075; A61K 7/32

[52] U.S. Cl. ............ 554/51; 554/59; 424/65; 424/70.31; 426/323; 426/332; 426/335; 252/89.1

[58] Field of Search ..................... 554/51, 59

[56] References Cited

U.S. PATENT DOCUMENTS

| | | | |
|---|---|---|---|
| 2,842,479 | 7/1958 | Jungermann | 554/59 X |
| 3,559,602 | 2/1971 | Johl et al. | 554/109 |
| 3,985,722 | 10/1976 | Yoshida et al. | 554/51 X |
| 4,148,926 | 4/1979 | Baker et al. | 554/51 X |
| 5,068,064 | 11/1991 | Proietto et al. | 554/51 X |

FOREIGN PATENT DOCUMENTS

| | | | |
|---|---|---|---|
| 0320976 | 6/1989 | European Pat. Off. | 554/59 |
| 512643 | 5/1982 | Spain. | |
| 518433 | 12/1982 | Spain. | |
| 1352420 | 5/1974 | United Kingdom | 554/51 |
| 2140297 | 11/1984 | United Kingdom | 554/59 |

OTHER PUBLICATIONS

Infante et al I, Chemical Abstracts, vol. 103, #22378a, 1985.
Dominguez et al, Chemical Abstracts, vol. 99, #122920a, 1983.
Infante et al II, Chemical Abstracts, vol. 119, 190 119990p, 1993.

*Primary Examiner*—Floyd D. Higel
*Attorney, Agent, or Firm*—Steinberg, Raskin & Davidson, P.C.

[57] ABSTRACT

The process of the invention is directed to the synthesis of cationic type surfactant compounds consisting of natural basic-character amino acids, and any of their homologs, suitably modified for the purpose of obtaining products having specific applications as antimicrobial (biocidal) agents. The process comprises a first step of esterification of an amino acid, and a second step of the condensation of a fatty acid chloride with an esterified amino acid derivative. Nontoxic reaction media and catalysts are used, and a final product free from impurities is obtained. The cost of the process of the invention is reduced from prior art processes due to the use of cheaper starting materials and simpler equipment.

15 Claims, No Drawings

PROCESS FOR THE SYNTHESIS OF CATIONIC SURFACTANTS COMPRISING ESTERIFICATION WITH BASIC CHARACTER AMINO ACIDS

This application is a 371 of PCT/ES95/00027 filed Mar. 8, 1995.

The present invention relates to a new process for obtaining cationic surfactant products, the hydrophilic portion of which consists of an esterified basic character amino acid and the hydrophobic portion thereof consists of a fatty acid linked to the α-amino group of the amino acid via an amide bond.

BACKGROUND OF THE INVENTION

The application of cationic surfactant compounds as antimicrobial agents has been studied extensively.

As background to the present patent application, the following patents may be mentioned: JP 7416005; JP 7505350; JP 723571; JP 7783942; JP 73118516; JP 8153280; GB 1352420, and U.S. Pat. No. 3,985,722.

There is a history of application of compounds of a similar nature in fields such as cosmetics (see Patent GB 1352420), dentrifices (JP 51023571) and hair conditioners (GB 2140297).

In Patents EP 320,976 and GB 1352420, the synthesis is described of compounds similar to the ones obtained in the process of the invention (such as pyrrolidinecarboxylate salts ). The synthesis process is carried out in a particular order and according to particular reaction conditions: condensation of the fatty acid with the amino acid in an organic/aqueous medium, subsequent esterification of the N-acylamino acid with the corresponding alcohol saturated with hydrochloric acid and lastly salt formation with pyrrolidinecarboxylate.

In U.S. Pat. No. 3,985,722, the acylating reactant is a mixture of the fatty acid and sulfur trioxide, the reaction being carried out in the presence of triethanolamine.

In Patent ES 512643, the preparation of the compounds which are the subject of the present application comprises a first step of esterification and a second step of condensation of an esterified amino acid derivative with a fatty acid, the fatty acid being used directly without derivatization and dicyclohexylcarbodiimide being employed as condensing agent.

SUMMARY OF THE INVENTION

The present invention involved a process for the synthesis of cationic surfactants derived from the condensation of fatty acids with esterified dibasic amino acids, of the formula:

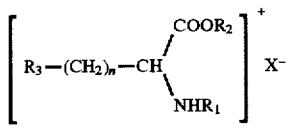

where:

$X^-$: can be: $Br^-$, $Cl^-$, $HSO_4^-$ [sic]

$R_1$: is a linear alkyl chain of a saturated fatty acid or hydroxy acid having 8 to 14 carbon atoms, linked to the α-amino group of the amino acid via an amide bond.

$R_2$: can be a linear or branched alkyl residue having 1 to 12 carbon atoms or an aromatic residue.

$R_3$: can be

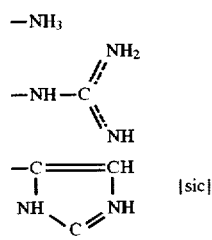

[sic]

it being possible for n to vary from 0 to 4, where the process comprises a first step of esterification of an amino acid, characterized in that, in a second step, condensation of a fatty acid chloride takes place with an esterified amino acid derivative.

The process to which this patent relates consists of at least two steps, which are as follows:

1.—Esterification of the carboxyl group of the α-amino acid with linear, branched or aromatic $C_1$–$C_{12}$ alcohols, using thionyl chloride as reagent and exploiting the heat of reaction in order to carry it out.

2.—Condensation of the $C_8$–$C_{14}$ fatty acid linear alkyl chain with the α-amino group starting from the corresponding acid chloride in an alkaline aqueous medium.

The present invention utilizes nontoxic starting materials and catalysts and provides a cationic surfactant which is free from impurities.

The present invention encompasses a method of using the cationic surfactant obtained according to the process described as an antimicrobial agent.

DESCRIPTION OF THE INVENTION

The objective of the present invention is to prepare cationic surfactants derived from basic character amino acids in good yield and state of purity from nontoxic starting materials and catalysts, the cost in energy terms being minimized and a final product free from impurities being obtained, with specific applications as antimicrobial agents.

The present invention relates to the preparation of molecules which correspond to the formula:

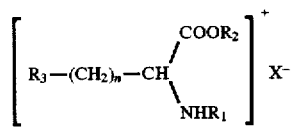

where:

$X^-$ can be $Br^-$, $Cl^-$, $HSO_4^-$ $R_1$ is a linear alkyl chain of a saturated fatty acid or hydroxy acid having 8 to 14 carbon atoms, linked to the α-amino group of the amino acid via an amide bond.

$R_2$ can be a linear or branched alkyl residue having 1 to 12 carbon atoms or an aromatic residue.

$R_3$ can be

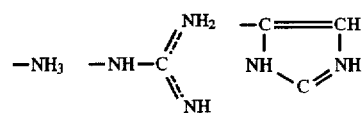

it being possible for n to vary from 0 to 4.

The starting materials used can be:

technical grade amino acids.
technical grade fatty acid chlorides.
deionized water.
technical grade caustic soda and hydrochloric acid.

The process to which this patent relates consists basically of two steps.

1.—Esterification of the carboxyl group of the α-amino acid with linear, branched or aromatic $C_1$–$C_{12}$ alcohols, using thionyl chloride as reagent and exploiting the heat of reaction in order to carry it out.

2.—Condensation of the $C_8$–$C_{14}$ fatty acid linear alkyl chain with the α-amino group starting from the corresponding acid chloride in an alkaline aqueous medium.

In the step of esterification of the carboxylic acid of an α-amino acid, any commercial amino acid may be used, preference being given to dibasic amino acids, especially L(+)-arginine.

The second step of condensation of the fatty acid chloride or hydroxy acid chloride with the amino acid ester is performed in an alkaline aqueous medium without the need to use any organic solvent. Said condensation is carried out at an alkaline pH, preferably at a pH of between 8 and 10.

The alkaline pH is obtained by adding an alkali metal hydroxide, preferably sodium or potassium hydroxide, to the aqueous medium.

When the condensation has been performed, the product is recovered by means of centrifugation of the precipitated product after adjusting the medium to a practically neutral pH, preferably to a pH of between 6 and 7, by adding an inorganic acid, preferably hydrochloric acid.

Preferably, in the process of the invention, the esterification of the amino acid with C1–C12 alcohols, especially ethanol, takes place by adding thionyl chloride to a suspension, prepared at room temperature, of arginine in alcohol.

The process of the invention differs from the previous processes both in the esterification step and in the condensation step.

In the esterification step, the same reactants and the same catalyst are used as in Patent ES 512643, but the reaction sequence is different. The reactants (arginine and ethanol) are not mixed simultaneously with the catalyst (thionyl chloride), instead the catalyst is added subsequently to the reactants. In this way, the reaction of the invention is exothermic, so that the heat evolved is exploited with a corresponding energy saving during this phase of the process.

In the condensation step, the components are different. Thus, for example, in Patent ES 512643. DMF (dimethylformamide), dicyclohexylcarbodiimide and a fatty acid are used, while, in the invention, water, caustic soda and a fatty acid chloride are used. This step thus entails a condensation of the fatty acid chloride in an aqueous medium, the hydrochloride of the corresponding derivative being separated.

Consequently the process of the invention differs substantially from the previous processes as regards the nontoxic starting materials and catalysts used and the freedom from impurities in the final products obtained, a very important discriminatory feature inasmuch as it eliminates the interference which said impurities may produce in the final application as antimicrobial agents. Due to the materials used, the cost of the process also proves lower and the equipment simpler.

The present invention also relates to the application of the products obtained by the above-mentioned process as antimicrobial (biocidal) agents.

The products described lack skin irritant effects and significant gastric ulcerogenic activity, are not mutagenic (according to the Ames test) at the doses at which they are normally used in their fields of application and possess $LD_{50}$ values via the oral route of greater than 2000 mg/kg. (The $LD_{50}$ is a way of expressing the toxicity of any product, and is defined as the minimum dose, expressed in mg of product under study per kg of test animal bodyweight, which produces the death of 50% of the animals which are the subject of the test).

The products described are capable of forming supramolecular aggregates of the micelle type, liquid crystals, emulsions and microemulsions in binary, ternary and quaternary systems, the technology of which is applicable to many industrial fields such as cosmetics, dermopharmacy or foodstuffs.

EXAMPLES

Several examples are detailed below:

One example of obtaining a product and four examples of application: two in the meat industry and two in cosmetics.

Example I

We shall describe the process for obtaining, on a laboratory scale, a specific product: the lauramide of L(+)-arginine ethyl ester monohydrochloride.

As mentioned in the description, the process consists of two steps.

FIRST STEP

Preparation of L(+)-arginine ethyl ester dihydrochloride

In a glass reactor of capacity 2 liters with a five-socket lid and provided with a mechanical stirrer, reflux condenser, nitrogen gas inlet, dropping funnel and thermometer, 1 equivalent of L(+)-arginine hydrochloride is suspended in 200 ml of essentially water-free ethyl alcohol at room temperature, and the stirrer is started.

1.3 equivalents of thionyl chloride are then added dropwise over a period of two hours, reflux being maintained by heating. When the mixture reaches the boiling point, it is stirred for a further three hours, after which the solvent is removed by evaporating it off at reduced pressure several times, with prior additions of dry ethanol.

SECOND STEP

Preparation of the lauramide of L(+)-arginine ethyl ester monohydrochloride

The above crude reaction product is dissolved in water and neutralized with aqueous sodium hydroxide, and the mixture is subsequently brought to pH 8–10 at which it is maintained for the remainder of the reaction while 1.1 equivalents of lauroyl chloride are added dropwise, the temperature of the mixture being maintained below 20° C. by means of an appropriate cooling bath with ethylene glycol.

When the addition is complete, stirring is maintained for a further two hours, the pH being finally adjusted to values of 6–7 with hydrochloric acid. Lastly, the crude reaction product is filtered off, a white solid of pearly appearance being obtained, of yield 80–85% W/W with respect to the product initially expected.

Example II

We shall describe the application of the product obtained according to the process described in Example I as preservative in the meat industry, specifically of cooked ham.

With the object of evaluating the antimicrobial activity of the product obtained according to the process described in Example I, a test was performed on an industrial scale in a cooked ham production plant, as explained below:

The product (the lauramide of L(+)-arginine ethyl ester monohydrochloride) is added into a 100-l reservoir containing injection brine for hams, in an amount such that it results in a dose of 2 g of product per 1000 g of treated ham.

According to the usual industrial methods, the hams are injected with said brine, massaging is then performed for 48 hours using vacuum drums and the hams are subsequently cooked (at 69° C. in the center of the piece), after which they are wrapped. From this point on, a microbiological study is carried out over four months, during which period the pieces have been subjected to extreme storage conditions.

The evaluation of the efficacy of the product as preservative of hams (through its antimicrobial effect) has been carried out by means of microbiological tests, the level of microbial (specifically bacterial, in this case) contamination present in the pieces being determined.

The method of determination is that of counting streaks on plates, total mesophilic aerobic bacteria, enterobacteriaceae and heterolactic microbiota being determined.

The results obtained at the fourth month are as follows:

|  | CFU/g | |
| --- | --- | --- |
|  | N.P. | W. Prod. |
| Total mesophilic aerobic | $2 \times 10^5$ | $1.5 \times 10^3$ |
| Enterobadteriaceae | $3.5 \times 10^3$ | absence |
| Heterolactic | $1 \times 10^2$ | absence |

(The results are expressed in colony forming units (CFU) (bacteria) per gram)

The column headed N.P. corresponds to product with no preservative; in the column headed W.Prod. the product which is the subject of the example has been added at the dose described.

From the results obtained, a clear picture emerges of the efficacy of the product, which significantly lowers the level of the first microorganism mentioned (to levels which are tolerable for the ham not to putrify) and eliminates them completely in the other two cases.

Example III

This example consists of a repetition of the previous test, injecting the hams with brine containing the product which is the subject of Example II (W.Prod. column) and, by way of comparison, in another group of hams, with brine containing a traditional chemical preservative based on potassium sorbate and propyl p-hydroxybenzoate (TP column).

The results obtained are as follows:

|  | CFU/g | |
| --- | --- | --- |
|  | N.P. | W. Prod. |
| Total mesophilic aerobic | $1 \times 10^3$ | absence |
| Enterobacteriaceae | absence | absence |
| Heterolactic | absence | absence | from which there emerges a better efficacy of the proposed product than that of the traditional chemical preservative used as reference. This is in agreement with the good properties of the proposed product, given, moreover, its safety features.

It should be noted that the absolute value of the counts may vary from one test to another, it being necessary to take into account the trends.

Example IV

We shall describe the application of the product in the cosmetic industry, specifically its use as preservative in the preparation of a shampoo.

An amount (5 Kg) of shampoo is prepared on a laboratory scale according to a conventional formulation, expressed in % w/w:

| | |
| --- | --- |
| 25% Sodium lauryl sulfate | 30% |
| Lauric diethanolamide | 5% |
| Preservative (the same as in Ex. I and II) | 0.04–0.05% |
| Deionized water | q.s. 100% |

(neither perfume nor colorant is included since these do not affect the preservation process).

Another similar amount of shampoo is prepared with the same formula but without preservatives for use as reference.

The antimicrobial activity of both is determined by means of an adaptation of the "challenge" test, in which samples of both shampoos are arranged, adding to all of them a combined inoculum of yeasts, bacteria and fungi of the following species and strains:

*Escherichia coli* (ATCC No. 9027)

*Staphylococcus aureus* (ATCC No. 8739)

*Pseudomonas aureoginosa* [sic] (ATCC No. 9077)

*Candida albicans* (ATCC No. 10231)

*Aspergillus niger* (ATCC No. 16404)

The test consists in contaminating a certain amount of the shampoo of the abovementioned samples by inoculating them with several known microorganisms, and seeing their development at a particular time and temperature (37° C. in our case).

In our case, the plate counts are performed at various incubation times, giving the results detailed below, from which the effectiveness of the product in the shampoo is clearly deduced (from the fall in the number of colonies) by comparing the shampoo with the reference not containing the product.

| | COLONIES /GRAM FORMULATION 1st inoculation | | | | | | | |
|---|---|---|---|---|---|---|---|---|
| INCUBATION TIME | 0 hours | | 24 hours | | 3 days | | 7 days | |
| SAMPLE | TNB | F & Y | TNB | F & Y | TNB | F & Y | TNB | F & Y |
| Reference (without preservatives) | $3 \times 10^6$ | $2 \times 10^5$ | $3 \times 10^6$ | $1 \times 10^4$ | $3 \times 10^6$ | $5 \times 10^2$ | $6 \times 10^6$ | <10 |
| With 0.4% of the product which is the subject of the example | $3 \times 10^6$ | $2 \times 10^5$ | <10 | <10 | <10 | <10 | <10 | <10 | where TNB = total number of bacteria
F & Y = number of fungi and yeasts

| | COLONIES /GRAM FORMULATION 1st inoculation | | | | | | | |
|---|---|---|---|---|---|---|---|---|
| INCUBATION TIME | 0 hours | | 24 hours | | 3 days | | 7 days | |
| SAMPLE | TNB | F & Y | TNB | F & Y | TNB | F & Y | TNB | F & Y |
| Reference (without preservatives) | $5 \times 10^7$ | $3 \times 10^5$ | $5 \times 10^7$ | $5 \times 10^4$ | $7 \times 10^7$ | $4 \times 10^3$ | $7 \times 10^7$ | $1 \times 10^3$ |
| With 0.4% of the product which is the subject of the example | $5 \times 10^7$ | $3 \times 10^5$ | $4 \times 10^4$ | $1 \times 10^2$ | <10 | <10 | <10 | <10 |

Example V

In this example, a test is performed of its efficacy as preservative in a deodorant which is presented in aerosol form and whose formulation, expressed in % w/w, is as follows:

| | |
|---|---|
| 1,2-Propylene glycol | 1% |
| Ethanol | 40% |
| Preservative (the same as in the previous ex.) | 0.4–0.5% |
| Deionized water | q.s. 100% |

(perfume is not included since it does not affect the preservation process; neither is the propellant included)

The antimicrobial activity is determined by measuring the halo of inhibition which are [sic] produced in the agar plate cultures of the following strains:

*Pseudomonas aureoginosa* (ATCC No. 9077)

*Staphylococcus aureas* (ATCC No. 8739)

*Escherichia coli* (ATCC No. 9027)

*Candida albicans (ATCC No.* 10231)

*Aspergillus niger*(ATCC No. 16404)

The plates are incubated in an incubator for 18 hours at 37° C.

The following results are obtained

| | DIAMETER OF THE HALO OF INHIBITION (+13 mm sample disk) | |
|---|---|---|
| MICROORGANISM UNDER STUDY | Sample with 0.4% of the preservative under study | Control sample (without preservative) |
| *Staphylocccccus aureus* | 30 | 13 |
| *Pseudomonas aureoginosa* | 28 | 13 |
| *Escherichia coli* | 26 | 13 |
| *Candida albicans* | 15 | 13 |
| *Aspergillus niger* | 20 | 13 |

The results show the efficacy clearly: in the control samples a halo of inhibition does not occur (13 mm does not count since this corresponds to the central sample-carrier disk), while those containing preservatives produce a substantial-sized halo.

We claim:

1. A process for the synthesis of cationic surfactants derived from the condensation of fatty acids with esterified basic character amino acids, of formula:

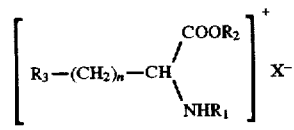

wherein:

$X^-$ is selected from the group consisting of $Br^-$, $Cl^-$, or $HSO_4^-$;

$R_1$ is a linear alkyl chain of a saturated fatty acid or hydroxy acid having from 8 to 14 carbon atoms, wherein said alkyl chain is linked to the α-amino group of the amino acid via an amide bond.

R₂ is a linear or branched alkyl radical having from 1 to 12 carbon atoms or is an aromatic radical; and R₃ is selected from the group consisting of:

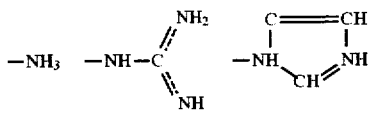

wherein n varies from 0 to 4, said process comprising a first step of esterification of an amino acid with $C_1$–$C_{12}$ alcohols, comprising adding thionyl chloride to a suspension of arginine in alcohol at room temperature to produce an esterified basic character amino acid derivative, said process further comprising a second step, condensing a fatty acid chloride with the amino group of said esterified basic character amino acid derivative.

2. Process according to claim 1, characterized in that said basic character amino acid derivative is L(+)-arginine.

3. Process according to claim 1, characterized in that the second step of condensation of said fatty acid chloride with the amino group of the esterified basic character amino acid derivative comprises using the chloride of said fatty acid, said saturated fatty acid having 8 to 14 carbon atoms.

4. The process according to claim 1, in which the condensation of the fatty acid chloride or hydroxy acid chloride with the amino acid ester takes place in an alkaline aqueous medium.

5. The process according to claim 3, in which the condensation of the fatty acid chloride or hydroxy acid chloride with the amino acid ester takes place in an alkaline aqueous medium.

6. The process according to claim 1, wherein the reaction medium is maintained at a pH of between 8 and 10 by adding sodium hydroxide.

7. The process according to claim 4, wherein the reaction medium is maintained at a pH of between 8 and 10 by adding sodium hydroxide.

8. The process according to claim 5, wherein the reaction medium is maintained at a pH of between 8 and 10 by adding sodium hydroxide.

9. The process according to claim 1, further comprising adjusting the pH of the product to between 6 and 7 by adding hydrochloride acid to obtain a crude reaction product, and centrifuging said crude reaction product to separate said cationic surfactant.

10. The process according to claim 2, further comprising adjusting the pH of the product to between 6 and 7 by adding hydrochloride acid to obtain a crude reaction product, and centrifuging said crude reaction product to separate said cationic surfactant.

11. The process according to claim 5, further comprising adjusting the pH of the product to between 6 and 7 by adding hydrochloride acid to obtain a crude reaction product, and centrifuging said crude reaction product to separate said cationic surfactant.

12. The process according to claim 3, further comprising adjusting the pH of the product to between 6 and 7 by adding hydrochloride acid to obtain a crude reaction product, and centrifuging said crude reaction product to separate said cationic surfactant.

13. The process according to claim 4, further comprising adjusting the pH of the product to between 6 and 7 by adding hydrochloride acid to obtain a crude reaction product, and centrifuging said crude reaction product to separate said cationic surfactant.

14. The process according to claim 6, further comprising adjusting the pH of the product to between 6 and 7 by adding hydrochloride acid to obtain a crude reaction product, and centrifuging said crude reaction product to separate said cationic surfactant.

15. A process according to claim 1 wherein said esterified basic character amino acid derivative is arginine ethyl ester dihydrochloride.

* * * * *